US009116104B2

(12) United States Patent  
Agar et al.

(10) Patent No.: US 9,116,104 B2  
(45) Date of Patent: Aug. 25, 2015

(54) METHOD AND APPARATUS FOR DETECTING WATER IN A FLUID MEDIA

(75) Inventors: Joram Agar, Grand Cayman (KY); Efim Metsner, Houston, TX (US)

(73) Assignee: Agar Corporation, Ltd., Grand Cayman (KY)

(*) Notice: Subject to any disclaimer, the term of this patent is extended or adjusted under 35 U.S.C. 154(b) by 1752 days.

(21) Appl. No.: 11/386,356

(22) Filed: Mar. 22, 2006

(65) Prior Publication Data

US 2007/0224692 A1 Sep. 27, 2007

(51) Int. Cl.  
*G01N 25/08* (2006.01)  
*G01N 27/22* (2006.01)  
*G01N 33/28* (2006.01)  
*G01N 25/00* (2006.01)  
*G01F 1/74* (2006.01)  
*G01F 1/712* (2006.01)  
*G01F 1/64* (2006.01)

(52) U.S. Cl.  
CPC ............ *G01N 27/22* (2013.01); *G01N 33/2823* (2013.01); *G01F 1/64* (2013.01); *G01F 1/712* (2013.01); *G01F 1/74* (2013.01)

(58) Field of Classification Search  
CPC ...... G01N 33/2823; G01N 27/22; G01F 1/74; G01F 1/66; G01F 1/712  
USPC .............. 436/39–40, 150; 324/323, 634, 640, 324/643, 664, 694; 73/152.06, 152.08, 73/152.14, 152.55, 614.3, 152.18  
See application file for complete search history.

(56) References Cited

U.S. PATENT DOCUMENTS

| 4,289,020 | A | | 9/1981 | Paap |
| 4,401,575 | A | | 8/1983 | Stewart et al. |
| 4,458,524 | A | | 7/1984 | Meador et al. |
| 4,607,014 | A | | 8/1986 | Nicksic et al. |
| 4,889,813 | A | | 12/1989 | Briining |
| 4,902,961 | A | | 2/1990 | De et al. |
| 5,224,372 | A | | 7/1993 | Kolpak |
| 5,266,800 | A | | 11/1993 | Mullins |
| 5,289,199 | A | * | 2/1994 | Viereck .......................... 343/745 |
| 5,424,595 | A | | 6/1995 | Preston et al. |
| 5,424,959 | A | | 6/1995 | Reyes et al. |
| 5,699,269 | A | | 12/1997 | Ashe et al. |
| 5,793,216 | A | | 8/1998 | Constant |
| 5,804,721 | A | * | 9/1998 | Yankielun et al. ......... 73/335.04 |
| 5,808,180 | A | | 9/1998 | Roussis et al. |

(Continued)

OTHER PUBLICATIONS

Yu et al. An improved approach for resonant measurements of complex permittivity of lossy liquids. 1999 IEEE Russia Conference: MIA-ME'99. pp. 34-39. (1999).*

(Continued)

*Primary Examiner* — Rebecca M Fritchman  
(74) *Attorney, Agent, or Firm* — Andrew W. Chu; Craft Chu PLLC

(57) ABSTRACT

An apparatus and method for measuring the concentrations of oil, water and/or hydrates in a multiphase production fluid flow comprises measuring the complex permitivities, both real and imaginary parts, of the flow at at least two frequencies. One dispersive and one non-dispersive frequency are used. In one embodiment at least three frequencies may be selected, one of which is below about 1 MHz while the other two are within the dispersive and non-dispersive ranges for water. In this embodiment water may be distinguished from hydrates and both measured simultaneously.

16 Claims, 5 Drawing Sheets

(56) References Cited

U.S. PATENT DOCUMENTS

| | | | |
|---|---|---|---|
| 6,028,235 | A | 2/2000 | Heinemann et al. |
| 6,267,849 | B1 | 7/2001 | Taylor et al. |
| 6,292,756 | B1 | 9/2001 | Lievois et al. |
| 6,307,191 | B1 | 10/2001 | Waycuilis |
| 6,343,652 | B1 | 2/2002 | Corre et al. |
| 6,459,995 | B1 | 10/2002 | Collister |
| 6,490,029 | B1 | 12/2002 | Cho et al. |
| 6,573,715 | B2 | 6/2003 | King et al. |
| 6,905,605 | B2 | 6/2005 | Klomp |
| 2004/0016284 | A1 | 1/2004 | Gysling et al. |
| 2004/0135585 | A1 | 7/2004 | Nagy |
| 2005/0030034 | A1 | 2/2005 | Ganesan |
| 2005/0267700 | A1* | 12/2005 | Gamache et al. ............... 702/65 |

OTHER PUBLICATIONS

Kirichenko et al. The resonant method for water solution complex permittivity. MSMW '04 Symposium Procedings. pp. 859-861. (Jun. 2004).*

Jakobsen et al. Dielectric measurements of gas hydrate formation in water-in-oil emulsions using open-ended coaxial probes. Meas. Sci. Technol. vol. 8. pp. 1006-1015. (1997).*

* cited by examiner

MS – measuring sensor (LCR Measuring Circuit)
RCMU – resonant circuit measurement unit
S – switch
C – measuring capacitor
L(*i*) – inductors
MF – multiphase fluid
*i* – index number for operational frequency
*i* = 1,2,3,...N $A_{max}$ – maximum signal from LCR resonant circuit
$F_r(i)$ – resonant frequency
i – index number of operational frequency
$\Delta F(i)$ – bandwidth of the resonant circuit
$Q(i)$ – Quality factor of the resonant circuit

METHOD AND APPARATUS FOR DETECTING WATER IN A FLUID MEDIA

BACKGROUND

1. Field of Invention

This invention relates to the field of methods of measuring water and hydrates content in production fluids. More particularly, it relates to methods and apparatuses for measuring water in multiphase production fluid flows.

2. Background Art

Many fluids, such as hydrocarbon production fluids, contain a certain proportion of water. Generally this water is in one of two forms, either as liquid water, or hydrocarbons hydrates. These hydrates are ice-like minerals that form at moderately low temperatures and high pressures of the deep sea and some land applications. They contain a molecule of hydrocarbons to which 4 or more molecule of water bond themselves in a symmetrical cages to form hydrate crystals. Regardless of form, however, the presence of water along with the more desired components of the production fluid, such as oil, is often problematic. If in liquid form, the water must eventually be removed in order to enable refining. If in hydrate form, the water plays a part in plugging pipelines and presenting transportation and storage difficulties.

Because of the significance of the presence of water in either form, it is frequently desirable to be able to first accurately measure it and detect in which state it is, liquid with or without hydrates solid particles. Such measurement is crucial to a number of subsequent decisions and operations adjustments, which may be of a financial, allocation, control or safety type. However, many of today's methods of determining the proportion of the so-called "water cut", i.e., the proportion of the production fluid which is water in either liquid or hydrate form, are inaccurate as each hydrocarbon has different permittivity and or density. So unless individual calibration is performed, large error levels may result that can be as high as 5 percent. Current water cut meters are particularly susceptible to this high error level. This inaccuracy is often unacceptable.

For example, one known method is to measure the water cut by measuring the permittivity properties of the mixture. Permittivity is a physical quantity that describes how an electric field affects, and is affected by, a medium, according to the ability of that medium to polarize in response to the field. This method, unfortunately, is subject to systematic error. This systematic error results from the differences in the complex permittivity of different crude oils. These crude oils may be of highly complex composition and may include, for example, aliphatic and aromatic hydrocarbons of varying polarities, and various isomers thereof; molecules containing heteroatoms such as nitrogen, oxygen, sulphur or metals; resins and asphaltenes containing a wide variety of chemical groups such as naphthalenic acids, carboxylic acids, phenols, pyridines, thiophenols, benzothiophenes, alkylphenols, thiophenes, and other compounds whose substituents contribute to a relatively high level of polarity; salts; and, of course, water. Prior art methods have, however, failed to fully acknowledge this complexity of composition by using only overall density in its determination of complex permittivity. This density is converted to a dry crude oil dielectric constant (also known as the real part of complex permittivity) based upon an API gravity chart for zero shift compensation. However, because it is possible for two different dry crude oils, of different compositions, to have the same density but different dielectric constants, the dielectric constant is likely to be incorrect for the composition as a whole. Thus, even extremely accurate measurements of crude oil density may result in a crude oil dielectric constant with an error equivalent to 0.7 to 1.0 percent of water cut value. This degree of error is considered to be very high in many applications. Importantly, this method is also generally unsuited to in-line use in multiphase flows of production fluid.

Another method, geared particularly toward use where hydrates are being formed, involves simply detecting water in conjunction with measuring fluid pressure and temperature, and then performing an appropriate thermodynamics calculation therefrom. The drawback to this indirect method is that chemically active additives, such as methanol, salt, glycol and some other substances, substantially affect these calculations. Other indirect methods include those that look at either the effects produced by the hydrates, or the properties and structure of the hydrates, from which quantification is calculated rather than actually measured. These methods include both laboratory scale and industrial scale methods, including those based upon an array of instrumentation such as nuclear magnetic resonance (NMR) spectroscopy, Raman spectroscopy, and mass spectroscopy, sonic attenuation and propagation, fiber optic technology, volume-pressure-time relations, volume resistivity, and the like. Use of calculations rather than actual measurement, however, again leaves significant room for error.

As should be evident from the volume of references identified hereto, the detection of water in whatever form in a fluid media has received significant attention by many researchers. Generally speaking, the focus of attention of such research centered on the properties of hydrates rather than devising practical instruments for detecting the formation of hydrates and measuring their concentration, without prior knowledge of the properties of the hydrocarbons and salinity of the water in the conduit.

Thus, what is needed in the art is a method and apparatus for directly measuring the amount of water, in either liquid or hydrate form, in a multiphase production fluid flow, which reduces the error that frequently results from previously known methods and/or apparatuses. What is also needed in the art is a method and apparatus than can provide accurate measurements of water cut in crude oil without advance knowledge of properties of a particular dry crude oil.

SUMMARY OF THE INVENTION

This invention teaches a method and the apparatus for measuring water cut in crude oil which does not depend on differences in dry oil properties: density, viscosity, permittivity, conductivity, etc. hence it is simple, reliable and inexpensive. From the prior art one can see that there is need for accurate, reliable, simple apparatus to detect and measure natural hydrates in multiphase flow in the pipeline, in tank or in any other vessel, Improved accuracy of water cut measurement may be achieved with this invention. In one non-limiting embodiment it is a method of measuring water or hydrate in production fluids. The method comprises measuring the real and imaginary parts of the complex permittivity of a production fluid including water or hydrate, and crude oil. This measurement is carried out via dielectric spectroscopy, at at least two different frequencies. One frequency is dielectrically non-dispersive, and other frequency is dielectrically dispersive. Thus, an accurate measurement of the proportion of the water cut to the crude oil may be made.

In another non-limiting embodiment, the invention is an apparatus for measuring water in production fluids. The apparatus comprises a means for measuring, using dielectric spectroscopy, the real and imaginary parts of the complex permittivity of a production fluid that includes water (e.g., liquid water and/or hydrate), and crude oil. This measurement is done at at least two different frequencies, one of which is dielectrically non-dispersive, and the other of which is dielectrically dispersive.

BRIEF DESCRIPTION OF THE FIGURES

For detailed understanding of the present invention, references should be made to the following detailed description of the preferred embodiment, taken in conjunction with the accompanying drawings, in which like elements have been given like numerals and wherein.

DETAILED DESCRIPTION OF THE INVENTION

Figure 1:
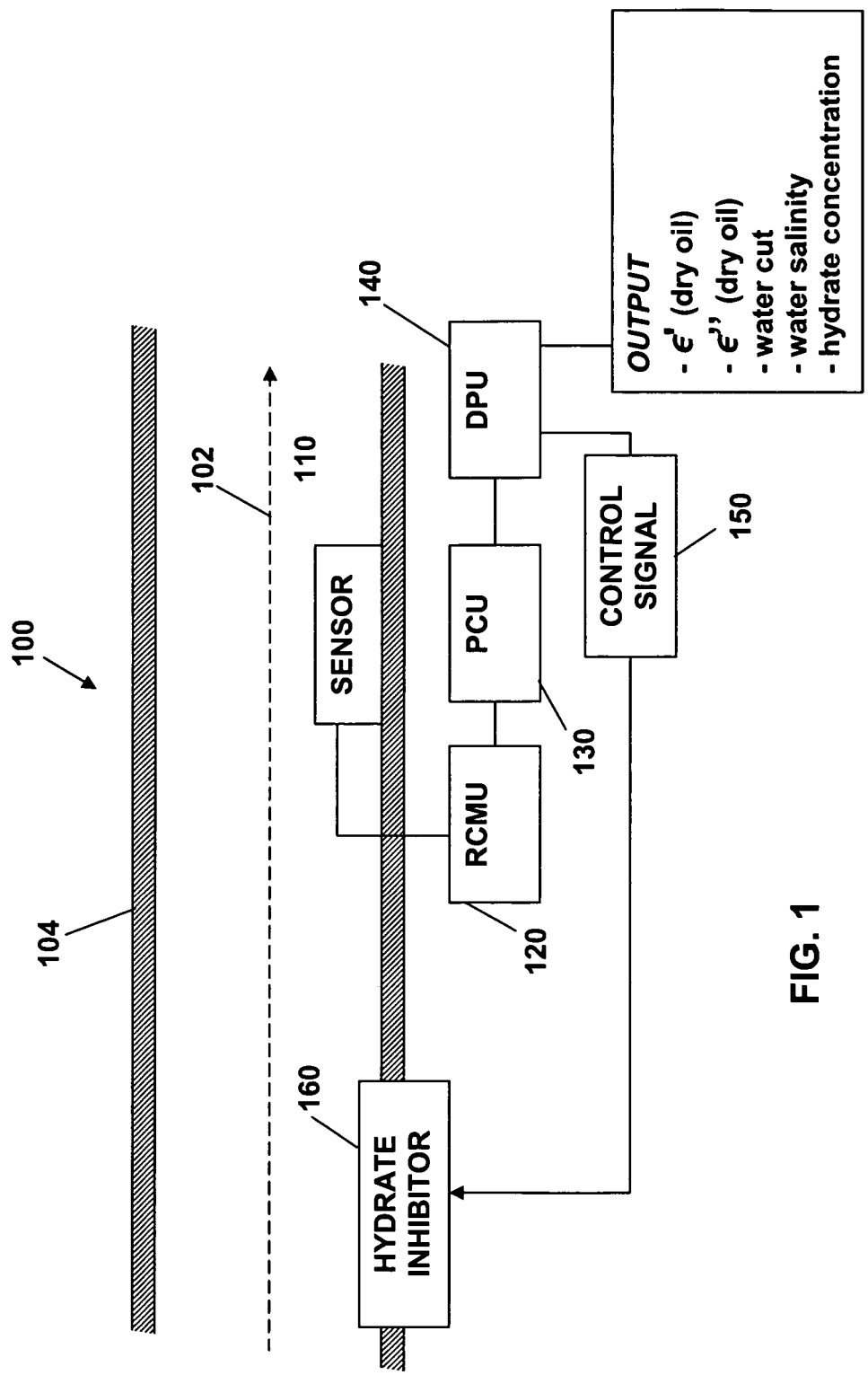
FIG. 1 schematically illustrates one embodiment of a hydrate detection and/or water cut measurement system made in accordance with the present invention.

In aspects, the present invention presents advancements over the prior art in that the teachings it allow direct and accurate measurement of the complex permittivity of a given multiphase fluid. In exemplary embodiments, the methods include measuring the complex permittivity at two or more selected frequencies. These methods are not dependent upon obtaining an API gravity upon which a dielectric constant will be based. Thus, these methods will determine permittivity with greater accuracy than prior art arrangements, which in turn, will lead to the determination of the amount of water or presence of hydrates with greater accuracy. While the teachings of the present invention can be advantageously adapted to a variety of applications, merely for simplicity the present invention will be discussed in the context of a flowing multiphase fluid hydrocarbon fluid such as crude oil. It should be appreciated that the present teachings can also be utilized in connection with standing in a tank or container and possibly with certain non-hydrocarbon fluids.

As will become apparent, the teachings of the present invention are well suited for industrial and commercial situations wherein accurate water cut measurements and/or hydrate detection are needed to maintain control and efficient flow regimes for a flowing crude oil. A few illustrative situations include a subsea flow line transporting fluid produced from a subterranean hydrocarbon formation and land based pipe lines transporting hydrocarbon fluids between two or more selected destinations. Such situations often have dynamic conditions wherein the chemical composition of the flowing fluid and flow parameters (e.g., pressure, temperature, etc.) can change unpredictably and within minutes. As can be appreciated, water measurement methods that rely upon tightly-controlled conditions and require prior knowledge of some aspect of the flowing fluid (e.g., chemical composition) will be difficult if not impossible to implement into a situation where chemistry and ambient conditions are subject to unpredictable changes. Advantageously, embodiments of the present invention do not require prior knowledge of the chemical composition of a flow liquid and can provide accurate water cut and hydrate detection even in a dynamic environment.

One illustrative method determines water cut and/or hydrate formation in a multiphase production fluid using dielectric spectroscopy. This method analyzes the dielectric behavior of the multiphase production fluid at both a dispersive and a non-dispersive frequency because water, whether in liquid form or in hydrate form, can influence the dielectric behavior of a multiphase production fluid in a manner than can be quantified. Dielectric dispersion is the frequency dependence of both the real and imaginary parts of a crude oil's complex permittivity. For general purposes the dielectric dispersion in crude oils may occur within a frequency range of from about 20 to about 200 megahertz (MHz). In contrast, the non-dispersive frequency range is generally from about 1 to about 10 MHz, while above about 200 MHz the dispersion behavior is considered to be non-regular. The method utilizes at least two measurements: a first measurement of selected parameters at a frequency between about 1 and about 10 MHz; and at a second measurement of the same parameters at a frequency between about 20 and about 200 MHz. As will be explained in greater detail below, additional measurements of dielectric permittivity can lead to improved accuracy of the water cut and hydrate detection.

These measurements taken at say frequency F1 and frequency F2 are used in calculations based upon the following four complex permittivity equations for mixtures of oil and water:

$$\epsilon'[\text{mixture}, F1] = f[\epsilon'(\text{oil}, F1), \epsilon''(\text{oil}, F1), \epsilon'(\text{water}, F1), \epsilon''(\text{water}, F1), \sigma(\text{water}), \text{water cut}] \quad \text{Equation 1}$$

$$\epsilon''[\text{mixture}, F1] = f[\epsilon'(\text{oil}, F1), \epsilon''(\text{oil}, F1), \epsilon'(\text{water}, F1), \epsilon''(\text{water}, F1), \sigma(\text{water}), \text{water cut}] \quad \text{Equation 2}$$

$$\epsilon'[\text{mixture}, F2] = f[\epsilon'(\text{oil}, F2), \epsilon''(\text{oil}, F2), \epsilon'(\text{water}, F2), \epsilon''(\text{water}, F2), \sigma(\text{water}), \text{water cut}] \quad \text{Equation 3}$$

$$\epsilon''[\text{mixture}, F2] = f[\epsilon'(\text{oil}, F2), \epsilon''(\text{oil}, F2), \epsilon'(\text{water}, F2), \epsilon''(\text{water}, F2), \sigma(\text{water}), \text{water cut}] \quad \text{Equation 4}$$

In the above equations:

$\epsilon'[\text{mixture}, F1]$ and $\epsilon''[\text{mixture}, F1]$=real and imaginary parts of permittivity of a mixture of crude oil and water at frequency F1;

$\epsilon'[\text{mixture}, F2]$ and $\epsilon''[\text{mixture}, F2]$=real and imaginary parts of permittivity of a mixture of crude oil and water at frequency F2;

$\epsilon'(\text{oil}, F1)$ and $\epsilon''(\text{oil}, F1)$=real and imaginary parts of permittivity of crude oil at frequency F1;

$\epsilon'(\text{oil}, F2)$ and $\epsilon''(\text{oil}, F2)$=real and imaginary parts of permittivity of crude oil at frequency F2;

$\epsilon'(\text{water}, F2)$ and $\epsilon''(\text{water}, F2)$=real and imaginary parts of permittivity of water at frequency F2;

$\epsilon'(\text{water}, F2)$ and $\epsilon''(\text{water}, F2)$=real and imaginary parts of permittivity of water at frequency F2;

$\sigma(\text{water})$=specific conductivity of salt water; and water cut=water content in the crude oil and water mixture.

The above equations express in a general form the relationships of the above-discussed properties. Specific models of complex permittivity of oil water mixtures described in Hasted J. B.—Aqueous Dielectrics, Chapman and Hall, London, 1973., which is hereby incorporated by reference for all purposes. Further discussion of the Bruggeman mixing formula and models describing complex permittivity of oil water mixtures are in U.S. Pat. No. 4,802,361, U.S. Pat. No. 6,655, 221, U.S. Pat. No. 6,831,470, U.S. Pat. No. 6,182,504 B1, U.S. Pat. No. 5,103,181, all of which are hereby incorporated by reference for all purposes.

In mixtures wherein hydrates are present, the above equations are modified by using the complex permittivity, both real and imaginary parts, of ice. Ice complex permittivity is not the same as that of liquid water, and thus the measurements at the different frequencies will be different. This is because the principal dielectric relaxation of pure ice takes place in a different frequency range. At frequencies below about 2 MHz, the real part of ice's complex permittivity varies from about 100 at a frequency of 500 hertz (Hz), down to about 5 at a frequency of about 100 kilohertz (kHz). The real part of its permittivity above 2 MHz is 3.15. The imaginary part of its complex permittivity has a maximum value of about 50 at a frequency of about 2-5 kHz. From this it will be seen that there is a very strong frequency dispersion at frequencies below 2 MHz, which means that the presence of hydrates may be easily distinguishable from that of liquid water.

Because of the differences in complex permittivity between liquid water and hydrates, then, it is possible to measure the presence of each, effectively at the same time, by simply taking a permittivity measurement at a third frequency, i.e., F3. This third frequency enables a simultaneous solution for the water cut and hydrates while still eliminating the zero shift-induced error of other methods. The third frequency may thus be desirably below about 1 MHz, and in some non-limiting embodiments may be significantly below about 1 MHz. In other non-limiting embodiments it may be from about 500 Hz to about 100 kHz The presence of hydrates results in a much larger complex permittivity (both real and imaginary parts) at frequency F1, whereas when hydrates are not present, the complex permittivity at both F1 and F2 will be the same. Thus, the concentration of hydrates is directly proportional to the frequency dispersion, i.e., if the hydrates concentration is higher, the frequency dispersion of the flow's complex permittivity will be greater.

In view of the above, the methods of the invention are well-suited to instrumental translation, i.e., devices and systems that are capable of taking the measurements and performing the calculations that result in ultimate determination of the presence of liquid water and/or hydrates in a multiphase production fluid flow. Such devices and systems may, in some non-limiting embodiments, be configured as a meter. An exemplary meter can be enabled, by means of design known to those skilled in the art of producing such devices, to obtain the frequency-based complex permitivities data on a suitably intermittent basis; calculate the concentrations therefrom; and provide or translate the information to an operator in a form that is easily understood. In some non-limiting embodiments, the information may be fed directly to control equipment of various types which are able to interpret the results and translate them into an instruction to change, or not change, some parameter relating to the multiphase production fluid flow.

For example, the apparatus of the present invention may be configured, in one non-limiting embodiment, to enable it to measure, simultaneously or consecutively, the flow's complex permittivity (both real and imaginary parts) at only two frequencies, F1 and F2, wherein F1 is lower than F2, in a situation where the goal is to determine the concentration of hydrates. In another non-limiting embodiment, the flow's complex permittivity is measured at only two frequencies, F2 and F3, wherein F3 is higher than F2, in a situation where the goal is to determine the concentration of water, i.e., the water cut. In still another non-limiting embodiment, the flow's complex permittivity is measured at at least three frequencies, F1, F2 and F3, in a situation where the goal is to determine both the water cut and the concentration of hydrates, such as where the composition of the flow may contain either, neither, or both.

Thus, the measured flow complex permitivities (both real and imaginary parts) may be described as comprising the following sets of comparative data:

Set 1: $\epsilon'$[mixture, F1], $\epsilon''$[mixture, F1], $\epsilon'$[mixture, F2], $\epsilon''$[mixture, F2]

Set 2: $\epsilon'$[mixture, F2], $\epsilon''$[mixture, F2], $\epsilon'$[mixture, F3], $\epsilon''$[mixture, F3]

A zero shift correction may then be easily made, either by manual or apparatus-based calculation, based on the equation:

$$\text{Zero shift correction} = f1[\epsilon'(\text{mixture}, F2), \epsilon'(\text{mixture}, F3)] \quad \text{Equation 5}$$

A water salinity correction may then be made according to the salinity of the water, illustrated by the equation:

$$\text{Water salinity correction} = f2[\epsilon'(\text{mixture}, F2), \epsilon''(\text{mixture}, F3)] \quad \text{Equation 6}$$

Finally, the hydrate concentration is shown by the equation:

$$\text{Hydrate concentration} = f3[\epsilon'(\text{mixture}, F1), \epsilon''(\text{mixture}, F1), \epsilon'(\text{mixture}, F2), \epsilon''(\text{mixture}, F2)] \quad \text{Equation 7}$$

In the case where an apparatus is used, hydrate concentration may alternatively be calculated according to the following equations, where K' and K" are instrumental parameters:

$$\text{Hydrate concentration} = K'[\epsilon'(\text{mixture}, F1)/\epsilon'(\text{mixture}, F2)-1] \quad \text{Equation 8}$$

$$\text{Hydrate concentration} = K''[\epsilon''(\text{mixture}, F2)/\epsilon''(\text{mixture}, F2)-1] \quad \text{Equation 9}$$

The following examples are provided merely to illustrate the invention for the purpose of increasing the reader's overall understanding of it. As such they represent merely potential embodiments of the invention and those skilled in the art will recognize that many modifications may be made within the scope of the invention as defined by the claims appended hereto.

Figure 2:
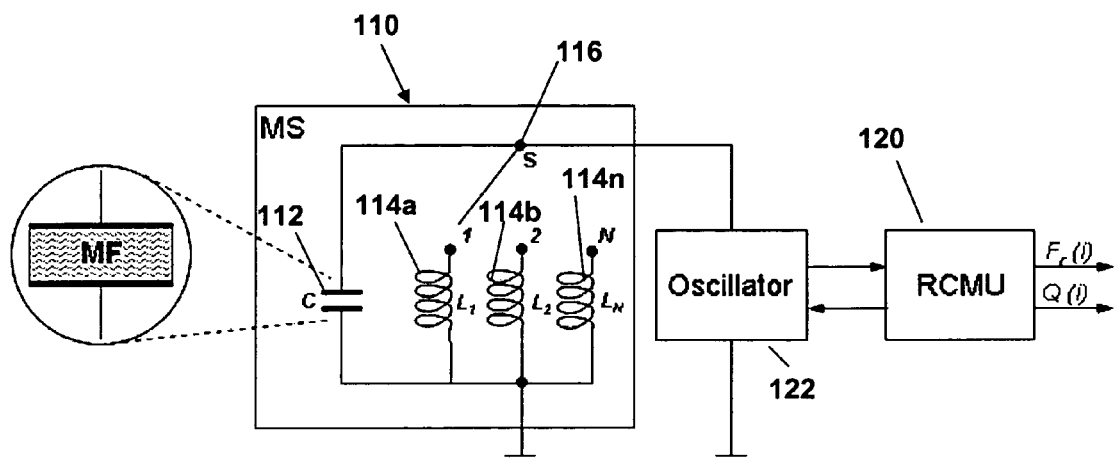
FIG. 2 schematically illustrates one embodiment of measurement sensor and measurement unit made in accordance with the present invention.
Figure 3:
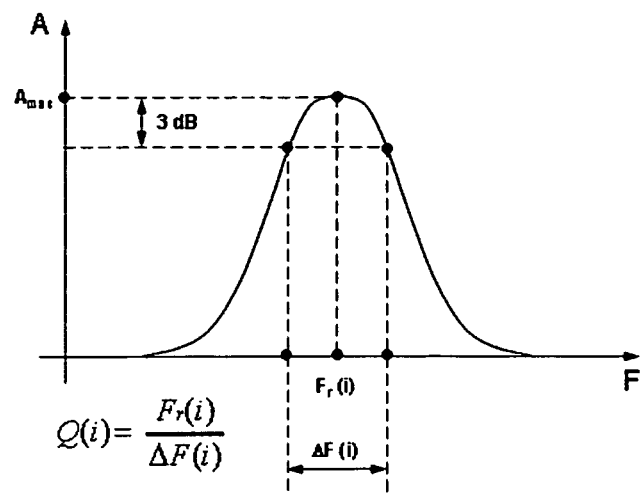
FIG. 3 shows an illustrative graph of frequency versus amplitude for an exemplary measurement data set obtained by the FIG. 2 embodiment.

Referring initially to FIG. 1, there is schematically illustrated a meter system 100 for detecting the presence of a hydrate and/or measuring a liquid water cut of a fluid 102 flowing through a conduit 104. In one embodiment, the system 100 includes a sensor 110, a measurement unit 120, a permittivity calculation unit 130, and a data processing unit 140. It should be understood that these components are shown separately merely to facilitate the discussion of the present teachings. Depending on the application, these components can be commonly housed or separately housed. Moreover, one processor in certain instances can be programmed to perform two or more of the tasks and functions described as done by separate units. The present invention encompasses all such embodiments and variations Referring now to FIGS. 1 and 2, the sensor 110 and measurement unit 120 cooperate to determine a resonant frequency and a Q-factor at two or more selected frequencies. A coaxial transmission line can be used to couple these two components. In one embodiment, the response of the sensor 110 is measured to collect a data set of frequencies and corresponding amplitudes. An illustrative response of the sensor 110 to a selected set of frequencies is shown in FIG. 3. Based on the FIG. 3 data set, the measurement unit 120 selects the resonant frequency F r establishes the bandwidth ($\Delta$ F) and calculates the corresponding Q factor. For example, the resonant frequency Fr(1) corresponds to the frequency when the signal from resonant circuit of the sensor 110 reaches the maximal value, as it is shown in FIG. 3, while the Q-factor Q(1) is calculated by dividing the resonant frequency Fr(1) on bandwidth of the RLC resonant circuit RLC—difference between frequencies at which the signal from RLC resonant circuit is reduced by 3 dB. The resonant frequency and corresponding Q factor are then transmitted to the Permittivity Calculation Unit 130.

In one embodiment, the sensor 110 includes a capacitor 112, a plurality of inductors 114a, 114b, 114n and a switch 116. As known, the resonant frequency of the 112 sensor 110 can change in response to the media in which the sensor 110, and in particular the capacitor 110, is immersed. In a conventional manner, a baseline or reference operating response of the sensor 110 is established for a known condition (e.g., a surrounding media of dry crude oil or air). Thereafter, the change in the behavior of the sensor 110 as the surrounding media changes can be characterized to determine one or more properties of the surrounding media. For example, because a surrounding crude oil-water mixture constitutes a part of the resonant circuit of the sensor 110, the complex permittivity of the fluid will affect the resonant frequency and Q-factor of the resonant circuit. The use of multiple inductors 114a-n, each of which has a different inductance, permits the sensor to be operated at a corresponding number of frequencies. The switch 116 selectively forms a circuit between the capacitor 112 and one of the inductors 114a-n. The sensor 110 can be constructed in a form of a probe or a cable that is inserted into the pipe 104. In another arrangement, the measuring capacitor 112 can be fitted into a spool piece that is in contact with multiphase flow or the sensor 110 can be integrated into a section of the pipe 104 itself. The present invention is not limited to any particular construction or configuration of the sensor 110.

The RCMU 120 uses an oscillator 122 to drive the sensor 110 across a plurality of frequencies. As the oscillator 112 scans or sweeps in the range of the corresponding resonant frequency, the amplitude-frequency dependence of the resonant circuit is measured. In one exemplary mode of operation, the switch 116 first forms a circuit between the capacitor 112 and the inductor 114a and sweeps across a set of frequencies to determine a first resonant frequency and associated Q factor. Next, the switch 116 forms a circuit between the capacitor 112 and the inductor 114b and sweeps across a set of frequencies to determine a second resonant frequency and associated Q factor. The same measuring process is repeated as many times and for as many operational frequencies (wavelengths) are used in the system. Of course, this operation can be repeated for less than all of the inductors 114 in the sensor 110.

The Permittivity Calculation Unit 130 calculates the complex permitivities (real part and imaginary part) of the fluid using the resonant frequency and associated Q-factor calculated at each of the two or more different frequencies. In one arrangement, a standard resonant circuit perturbation technique is used to calculate complex permittivity of a crude oil—water mixture. Resonant frequency values for air, standard certified fluid and measured fluid are used to calculate real part of the complex permittivity of the mixture. Values of Q-factor for air, standard certified fluid and measured fluid are used to calculate imaginary part of the complex permittivity of the mixture. The calculated complex permitivities (real part and imaginary part) are thereafter transmitted to the Data Processing Unit 140.

Figure 4:
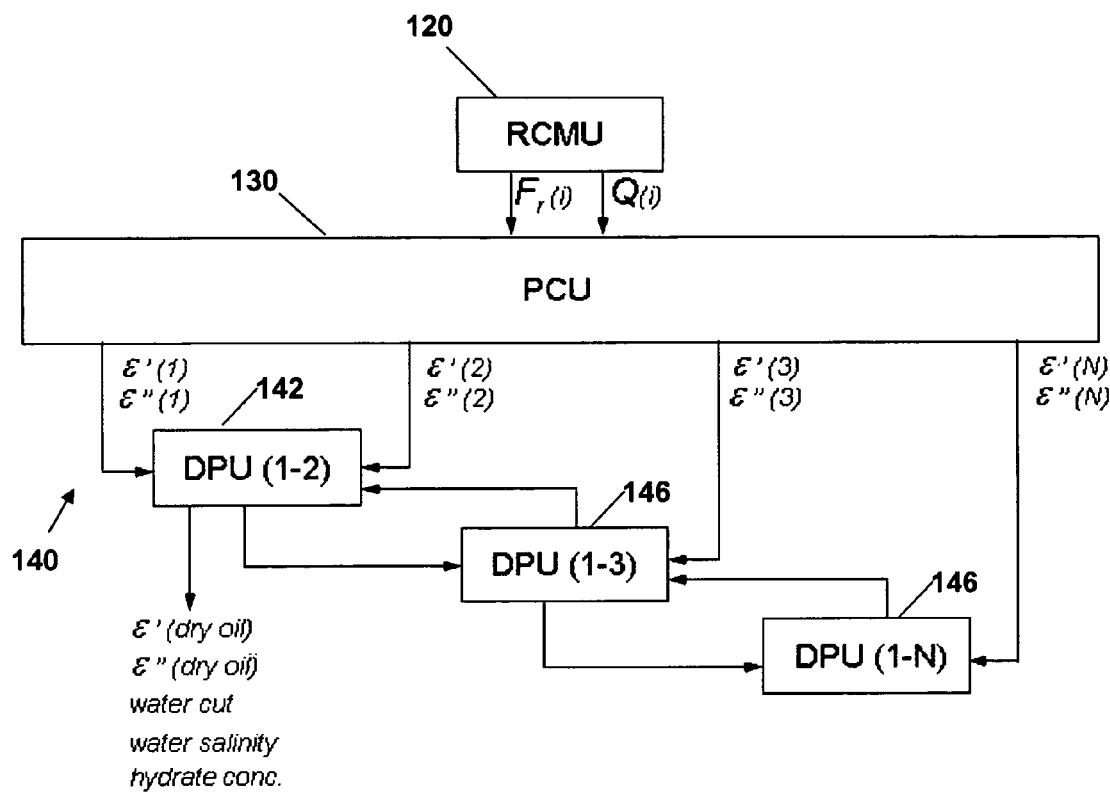
FIG. 4 illustrates a block diagram of one embodiment of a data processing unit made in accordance with the present invention.

The Data Processing Unit 140 calculates values of one or more properties or characteristics of the fluid. For example, the DPU 140 can calculate complex permittivity of dry oil (real and imaginary parts), water cut, water salinity, and hydrate concentration. Referring now to FIG. 4, there is shown a block diagram of an illustrative configuration of the Data Processing Unit 140. In the shown arrangement, DPU 142 processes the values of mixture complex permittivity (real and imaginary parts) measured at two operational frequencies (wavelengths) F(1) and F(2). DPU 144 processes the values of mixture complex permittivity [real and imaginary parts measured at three operational frequencies (wavelengths) F(1), F(2), F(3). More generally, the DPU 146 processes the values of mixture complex permittivity [real and imaginary parts] measured at N operational frequencies (wavelengths) F(1), F(2), . . . F(N). The final outputs of the combined Data Processing Unit [DPU] are complex permittivity of dry oil [real and imaginary parts], water cut, water salinity, hydrate concentration. The DPU 144 can include one or more processors programmed with complex permittivity models such as equations one to eight described above.

The measuring unit 120, the permittivity calculation unit 130 and the data processing unit 140 can apply one or more correction factors to account for changes in the prevailing environmental conditions. For instance, a temperature correction can be applied as needed to temperature-sensitive values. The system 100 can include sensors (not shown) that measure temperature, pressure or other parameters that could influence the measured values.

Referring back to FIG. 1, some embodiments of the present invention can be advantageously utilized to control hydrate formation in a fluid conduit or container. For example, the DPU 140 can be programmed to transmit control signals 150 to an inhibitor 160 positioned along the pipe 104. In response to the control signals 150, the inhibitor 160 can alter the flow environment, e.g., by adjusting chemistry or adding thermal energy, to inhibit the formation of hydrates. Under some conditions, hydrates can form and accumulate in a manner of minutes, which could make it difficult if not impossible for human intervention or control over the inhibitor 160. Conventionally, the inhibitor 160 is operated at a level selected to inhibit hydrate formation regardless of whether hydrates have been detected. For instance, conventionally, the inhibitor 160 can continuously inject a preset amount of a chemical inhibitor into the fluid stream 102. With embodiments of the present invention, the operation of the inhibitor 160 can be optimized. In one arrangement, the DPU 160 can be programmed to operate the inhibitor 160 to inject no or very little inhibitor when no hydrates are detected and to operate the inhibitor 160 to inject a greater amount of inhibitor when a hydrate is detected. In another arrangement, the DPU 160 can be configured to operate the inhibitor 160 such that an hydrate inhibiting fluid is injected in an amount proportional to the amount of hydrate detected.

While chemical inhibitors are commonly utilized, other inhibitors could include devices that add thermal energy to the fluid stream or perturb the fluid stream or pipe to shake loose hydrates. Still other inhibitors can include devices that change pipeline operating conditions (fluid pressure and temperature) and remove water from the flow prior to pipeline transportation.

Furthermore, because embodiments of the present invention are compact and have a relatively simple construction, certain embodiments can be made portable or mobile for use in diagnostic evaluation of pipelines.

Figure 5:
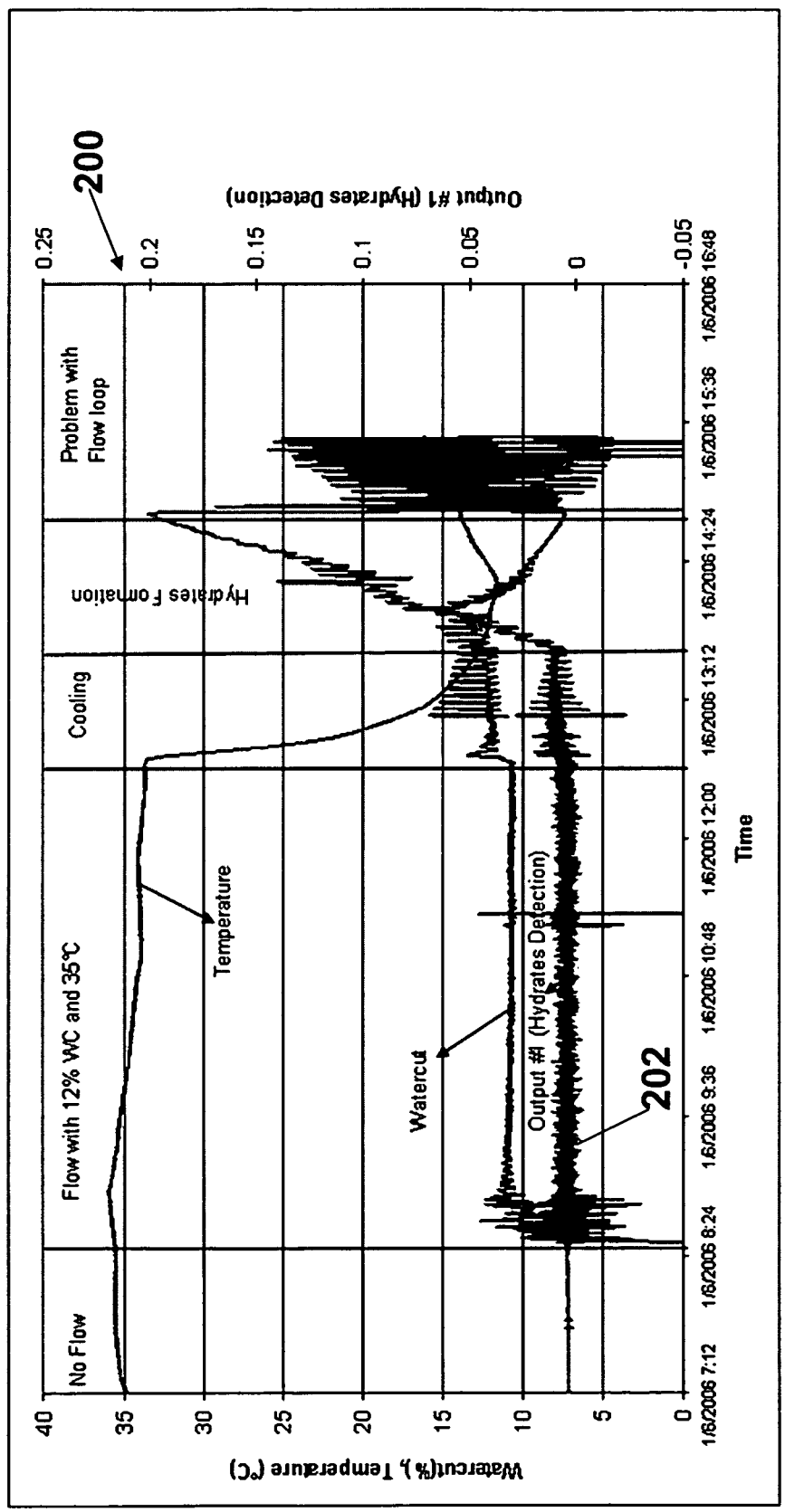
FIG. 5 is a graph showing the relationship of parameters measured at two frequencies to water in a fluid media.

Referring now to FIG. 5, there is shown a graph 200 illustrating the relationship of the measured values a real part of complex permittivity taken at two frequencies and the determinations of water cut and hydrate formation based on such measurements. In FIG. 5, output 202 is a ratio of e'L/e'H.

Where:
e'L=e' at a selected low frequency (e.g., 100 KHz); and
e'H=e' at a selected high frequency (e.g., 10 MHz)

As can be seen, the strategic use of multiple frequencies and the selection of frequencies in a dispersive and non-dispersive regions provides, among other things, a clear indication as to the presence and amount of hydrates, the water cut, and the temperature at which the hydrates start forming. Indeed, the strong correlation of the output 1 with change in hydrate allows one to see the percent of water in oil decrease as some of the water in the liquid phase has been converted to solid hydrates. It should also be noted that the measurement of water cut utilizing the teachings of the present invention is not affected the temperature or the flow rate.

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

What is claimed is:

1. A method of detecting hydrates in a multiphase fluid, comprising:
    applying energy waves at a plurality of frequencies to the multiphase fluid;
    determining a first most resonant frequency within a first resonant frequency range for a first resonant circuit coupled to the multiphase fluid to determine a first resonant frequency;
    measuring a parameter of said multiphase fluid dependent upon frequency at said first most resonant frequency when said first resonant circuit is coupled to the multiphase fluid;
    determining a second most resonant frequency within a second resonant frequency range for a second resonant circuit coupled to the multiphase fluid;
    measuring said parameter of said multiphase fluid at said second most resonant frequency when said second resonant circuit is coupled to the multiphase fluid; and
    determining a presence of hydrates in said multiphase fluid, hydrates and water in said multiphase fluid, water in said multiphase fluid, and no hydrates and no water in said multiphase fluid based on said parameter, said first most resonant frequency, and said second most resonant frequency,
    wherein measurements of said parameter of said multiphase fluid, said first most resonant frequency of said multiphase fluid, and said second most resonant frequency of said multiphase fluid are interrelated,
    wherein said first most resonant frequency range is selected from a range corresponding to said multiphase fluid being complex dielectric non-dispersive, and
    wherein said second most resonant frequency range is selected from a range corresponding to said multiphase fluid being complex dielectric dispersive.

2. The method of detecting hydrates, according to claim 1, wherein each resonant circuit is comprised of a capacitor.

3. The method of detecting hydrates, according to claim 1, wherein said parameter at said first most resonant frequency relates to a corresponding quality factor of said first resonant circuit in said multiphase fluid, said parameter at said second most resonant frequency also relating to a corresponding quality factor of said second resonant circuit in said multiphase fluid.

4. The method of detecting hydrates, according to claim 1, wherein said parameter is comprised of at least one of a group consisting of: water cut, water salinity, and hydrate concentration.

5. The method of detecting hydrates, according to claim 1, wherein said parameter is complex permittivity, said complex permittivity having a real part and an imaginary part.

6. The method of detecting hydrates, according to claim 5, wherein each real part of said complex permittivity corresponds to a measurement at said first most resonant frequency within said first resonant frequency range for said first resonant circuit and to a measurement at said second most resonant frequency within said second resonant frequency range for said second resonant circuit, respectively, and wherein each imaginary part corresponds to a quality factor determined from said first most resonant frequency of said first resonant circuit in said multiphase fluid and a quality factor determined from said second most resonant frequency of said second resonant circuit in said multiphase fluid, respectively.

7. The method of detecting hydrates, according to claim 1, further comprising the steps of:
    determining a third most resonant frequency within a third resonant frequency range for a third resonant circuit coupled to said multiphase fluid;
    measuring said parameter of said fluid media at said third most resonant frequency when said third resonant circuit is coupled to said multiphase fluid; and
    determining a presence of hydrates in said multiphase fluid, hydrates and water in said multiphase fluid, water in said multiphase fluid, and no hydrates and no water in said multiphase fluid based on said parameter, said first most resonant frequency, said second most resonant frequency, and said third most resonant frequency,
    wherein said parameter of said multiphase fluid, said first most resonant frequency of said multiphase fluid, said second most resonant frequency of said multiphase fluid, and said third most resonant frequency of said multiphase fluid are interrelated, and
    wherein said third resonant frequency range is selected from a range corresponding to said multiphase fluid being complex dielectric non-dispersive.

8. The method of detecting hydrates, according to claim 7, wherein said parameter is comprised of at least one of a group consisting of: water cut, water salinity, and hydrate concentration.

9. A method of detecting hydrates in a hydrocarbon production fluid, comprising:
    applying energy waves at a plurality of frequencies to the hydrocarbon production fluid;
    determining a first most resonant frequency within a first resonant frequency range for a first resonant circuit coupled to the production fluid;
    measuring real and imaginary parts of complex permittivity of said production fluid at said first most resonant frequency when said first resonant circuit is in the production fluid;
    determining a second most resonant frequency within a second resonant frequency range to for a second resonant circuit coupled to the production fluid;
    measuring real and imaginary parts of complex permittivity of the production fluid at said second most resonant frequency when said second resonant circuit is in the production fluid;

wherein said first resonant frequency range is selected from a range corresponding to said production fluid being complex dielectric non-dispersive, wherein said second resonant frequency range is selected from a range corresponding to said production fluid being complex dielectric dispersive, and wherein said real and imaginary parts of complex permittivity of said production fluid, said first most resonant frequency of said production fluid, and said second most resonant frequency of said production fluid are interrelated; and determining a presence of hydrates in said hydrocarbon production fluid, hydrates and water in said hydrocarbon production fluid, water in said hydrocarbon production fluid, and no hydrates and no water in said hydrocarbon production fluid based on said complex permittivity, said first most resonant frequency, and said second most resonant frequency.

10. The method of detecting hydrates, according to claim 9, wherein said first resonant frequency range comprises a range of approximately 1 MHz to 10 MHz.

11. The method of detecting hydrates, according to claim 9, wherein said second resonant frequency range comprises a range of approximately 10 MHz to 200 MHz.

12. The method of detecting hydrates, according to claim 9, further comprising the steps of:

determining a third most resonant frequency within a third resonant frequency range for a third resonant circuit coupled to the production fluid;

measuring real and imaginary parts of complex permittivity of the production fluid at said third most resonant frequency when said third resonant circuit is in the production fluid;

wherein said third resonant frequency range is selected from a range corresponding to said multiphase fluid being complex dielectric non-dispersive, and wherein said real and imaginary parts of complex permittivity of said production fluid, said first most resonant frequency of said production fluid, said second most resonant frequency of said production fluid, and said third most resonant frequency of said production fluid are interrelated; and determining a presence of hydrates in said hydrocarbon production fluid, hydrates and water in said hydrocarbon production fluid, water in said hydrocarbon production fluid, and no hydrates and no water in said hydrocarbon production fluid based on said complex permittivity, said first most resonant frequency, said second most resonant frequency, and said third most resonant frequency.

13. The method of detecting hydrates, according to claim 12, wherein said third most resonant frequency is less than said first most resonant frequency and said second most resonant frequency.

14. The method of detecting hydrates, according to claim 12, wherein said third most resonant frequency is more than said first most resonant frequency and said second most resonant frequency.

15. The method of detecting hydrates, according to claim 12, wherein said first resonant frequency range comprises a range of approximately 500Hz to 500KHz, and wherein said second resonant frequency range comprises a range of approximately 1 MHz to 200 MHz.

16. The method of detecting hydrates, according to claim 12, wherein said first resonant frequency range comprises a range of approximately 1 MHz to 10 MHz, wherein said second resonant frequency range comprises a range of approximately 20 MHz to 200 MHz, and wherein said third resonant frequency range comprises from a range of approximately 500 Hz to 2500 MHz.

* * * * *